United States Patent

Furukawa et al.

[11] Patent Number: 5,852,048
[45] Date of Patent: Dec. 22, 1998

[54] ESTER COMPOUND AND A PESTICIDAL AGENT CONTAINING THE SAME AS AN ACTIVE INGREDIENT

[75] Inventors: Takashi Furukawa; Kazunori Tsushima; Tomonori Iwasaki; Hirosi Kisida, all of Hyogo; Mikako Nakamachi; Yoji Takada, both of Osaka, all of Japan

[73] Assignee: Sumitomo Chemical Company, Limited, Osaka, Japan

[21] Appl. No.: 609,624

[22] Filed: Mar. 1, 1996

[30] Foreign Application Priority Data

Mar. 1, 1995 [JP] Japan .................... 7-041890

[51] Int. Cl.$^6$ ............ A61K 31/415; C07D 249/12
[52] U.S. Cl. .......................... 514/384; 548/263.2
[58] Field of Search ............. 548/263.2; 514/384

[56] References Cited

U.S. PATENT DOCUMENTS

| | | | |
|---|---|---|---|
| 4,542,142 | 9/1985 | Martel et al. | 514/345 |
| 4,859,230 | 8/1989 | Blume et al. | 548/263.2 |
| 5,310,751 | 5/1994 | Babin et al. | |

FOREIGN PATENT DOCUMENTS

| | | |
|---|---|---|
| 0 033 163 | 8/1981 | European Pat. Off. . |
| 0 041 021 | 12/1981 | European Pat. Off. . |
| 0050534 | 4/1982 | European Pat. Off. . |
| 57-126447 | 8/1982 | Japan . |
| 57-158765 | 9/1982 | Japan . |
| 1156943 | 6/1989 | Japan . |

OTHER PUBLICATIONS

*Database WPI*, Week 7838, Derwent Publications Ltd., London, G.B., AN 78–67608A;XP002009483 (JP–A–53 092 768—Aug. 15, 1978).

*Database WPI*, Week 8245, Derwent Publications Ltd., London, GB; AN 82–96032E;XP002009481 (JP–A–57 158 765—Sep. 30, 1982).

*Primary Examiner*—Patricia L. Morris
*Attorney, Agent, or Firm*—Sughrue, Mion, Zinn, Macpeak & Seas, PLLC

[57] ABSTRACT

There is disclosed an ester compound of the formula (I),

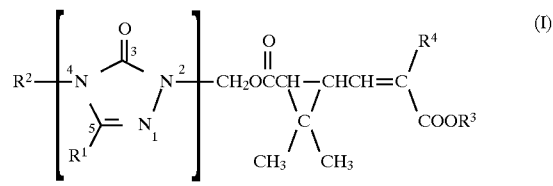

wherein $R^1$ represents a methyl group or a hydrogen atom, $R^2$ represents a proparqyl group or an allyl group, and $R^3$ represents a ($C_1$–$C_5$)alkyl group, a ($C_1$–$C_5$)haloalkyl group or a ($C_3$–$C_5$)cycloalkyl group and $R^4$ represents a halogen atom or a hydrogen atom, and a pesticide containing the same as an active ingredient.

9 Claims, No Drawings

ESTER COMPOUND AND A PESTICIDAL AGENT CONTAINING THE SAME AS AN ACTIVE INGREDIENT

FIELD OF THE INVENTION

The present invention relates to an ester compound and a pesticidal agent containing the same as an active ingredient.

DESCRIPTION OF THE RELATED ART

Hitherto, it is described, for example, in Japanese Patent Kokai (Laid-open)No. Sho 57-158765 that a certain kind of ester compounds is used as an active ingredient of pesticidal agents. However, those compounds are not always satisfactory in terms of pesticidal activities.

In view of the situation described above, the present inventors have extensively studied to find a compound having good pesticidal activity, and have found that an ester compound of the following formula (I) has good pesticidal activity.

SUMMARY OF THE INVENTION

That is, the present Invention provides an ester compound of the formula (I) (hereinafter referred to as present compound):

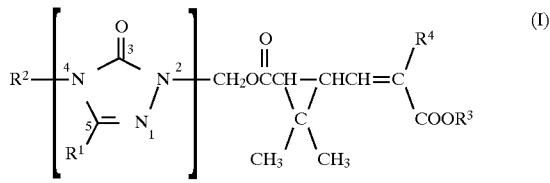

wherein $R^1$ represents a methyl group or a hydrogen atom, $R^2$ represents a propargyl group or an allyl group, and $R^3$ represents a $(C_1-C_5)$alkyl group, a $(C_1-C_5)$haloalkyl group or a $(C_3-C_5)$cycloalkyl group and $R^4$ represents a halogen atom or a hydrogen atom, and a pesticidal agent containing the same as an active ingredient.

DESCRIPTION OF THE PREFERRED EMBODIMENT

The $(C_1-C_5)$alkyl group for $R^3$ includes a methyl group, an ethyl group, a propyl group, an isopropyl group, a butyl group, a tert-butyl group and the like; the $(C_1-C_5)$haloalkyl group for $R^3$ includes a 2,2,2-trifluoroethyl group, a chloroethyl group and the like, and the $(C_3-C_5)$cycloalkyl group for $R^3$ includes a cyclopropyl group, a cyclobutyl group, a cyclopentyl group and the like.

The halogen atom for $R^4$ includes a fluorine atom, a chlorine atom, a bromine atom and the like.

In terms of pesticidal activity, $R^2$ in the formula (I) is preferably a propargyl group. $R^3$ is preferably a $(C_1-C_3)$ alkyl group such as an ethyl group, a $(C_1-C_3)$haloalkyl group such as 2,2,2-trifluoro-1-1-(trifluoromethyl)ethyl group, 2,2,2-trifluoroethyl group and the like, or the $(C_3-C_5)$ cycloalkyl group such as a cyclopropyl group. $R^4$ is preferably a halogen atom, more preferably a fluorine atom.

When $R^1$ is a methyl group, substitution position of $R^2$ on the triazolone ring is preferably 4-position. When $R^1$ is a hydrogen atom, substitution position of $R^2$ on the triazolone ring is preferably 2-position.

The present compound includes stereoisomers such as optical isomers designated as 1R-cis, 1R-trans, 1S-cis and 1S-trans resulting from an asymmetric carbon atom of cyclopropane ring moiety, geometrical isomers designated as E and Z resulting from a double bond to which $COOR^3$ is bonded, regio-isomers resulting from alcohol moiety such as one having $R^2$ on the 4-position of the triazolone ring and one having $R^2$ on the 2-position of the triazolone ring, and a mixture thereof in an optional ratio.

In the present compounds, cyclopropane ring moiety having (1R, cis) configuration is preferred. When cyclopropane moiety has said cis-configuration, a compound of which $COOR^3$ and cyclopropane take cis configuration with regard to the double bond to which $COOR^3$ is bonded, i.e. when $R^4$ is a halogen atom, designated as (E) configuration, or when $R^4$ is a hydrogen atom, designated as (Z) configuration, is preferred.

The present compound can be produced, for example, by the following method, which comprises reacting a carboxylic acid compound of the formula II:

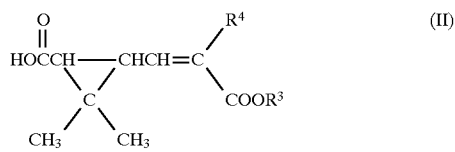

wherein $R^3$ and $R^4$ are the same as defined above or its reactive derivative, with an alcohol compound of the formula III:

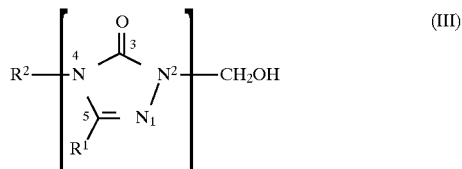

wherein $R^1$ and $R^2$ are the same as defined above. In this process 1 mole of the carboxylic acid (II) and 1 to 1.5 moles of the alcohol compound (III) are usually used.

The carboxylic acid compound of the formula (II) or its reactive derivative includes, for example, acid halogenide and acid anhydride, and acid chloride is preferably used.

When the carboxylic acid compound itself of the Formula (II) is reacted with the alcohol compound of the Formula (III), the reaction is usually carried out in the presence of a dehydrating agent such as dicyclohexylcarbodiimide(DCC) or 1-ethyl-3-(3-dimethylaminopropyl)carbodiimide hydrochloride(WSC) in an inert organic solvent such as dichloromethane, tetrahydrofurane(THF), benzene or toluene. An organic base such as pyridine, triethylamine, 4-dimethylaminopyridine or diisopropylethylamine may be allowed to coexist in this reaction. The reaction temperature is usually −10° C. to +100° C. or the boiling point of the organic solvent employed, preferably 0° C. to 30° C.

The reaction of the carboxylic acid chloride of the carboxylic acid compound of the Formula II and the alcohol compound of the Formula III is usually carried out in the presence of an organic base such as pyridine, triethylamine or 4-dimethylaminopyridine in an inert organic solvent such as dichloromethane, THF, benzene or toluene. The reaction temperature is usually −10° C. to 100° C. or the boiling point of the organic solvent employed, preferably 0° C. to +30° C.

After compeletion of the reaction, the reaction solution is subjected to a usual post-treatment such as an extraction with an organic solvent, washing and/or concentration to isolate the desired compound, and may be further purified by a usual procedure such as chromatography, if necessary.

The carboxylic acid compound of the formula (II) can be produced according to methods as described in Kokai(Laid open) Sho 57-126447, European Patent 0050534 or Kokai (Laid-open) Hei 1-156943.

The other intermediate alcohol compound of the formula (III) can be produced according to a method as described in Kokai Sho 57-158765.

Tables 1 and 2 show the examples of the present compounds.

TABLE 1

$$R^2-\overset{4}{\underset{\underset{R^1}{\overset{5}{\diagdown}}=N_1}{N}}\overset{O}{\overset{\|}{\underset{3}{C}}}-N^2-CH_2OCCH-CHCH=C\diagup\overset{R^4}{\underset{COOR^3}{\diagdown}}$$

| R¹ | R² | R³ | R⁴ |
|---|---|---|---|
| CH₃ | CH=CCH₂ | C₂H₅ | F |
| CH₃ | CH=CCH₂ | C₂H₅ | H |
| CH₃ | CH=CCH₂ | cyclopropyl | F |
| CH₃ | CH=CCH₂ | CH(CF₃)₂ | H |
| CH₃ | CH=CCH₂ | C₂H₅ | Cl |
| CH₃ | CH=CCH₂ | CH₃ | F |
| CH₃ | CH=CCH₂ | CH₂CF₃ | H |
| CH₃ | CH₂=CHCH₂ | C₂H₅ | F |

TABLE 2

$$R^2-\overset{2}{\underset{\underset{R^1}{\overset{}{\diagdown}}_1N=\overset{5}{\diagup}}{N}}\overset{O}{\overset{\|}{\underset{3}{C}}}-N^4-CH_2OCCH-CHCH=C\diagup\overset{R^4}{\underset{COOR^3}{\diagdown}}$$

| R¹ | R² | R³ | R⁴ |
|---|---|---|---|
| H | CH=CCH₂ | C₂H₅ | F |
| H | CH=CCH₂ | cyclopropyl | F |
| H | CH=CCH₂ | CH(CF₃)₂ | H |
| H | CH₂=CHCH₂ | C₂H₅ | F |

The present compound exhibits a good pesticidal activity, for example, against noxious insects and acarines listed below. Noxious insect pests such as:

Hemiptera:

Planthoppers (Delphacidae) such as small brown planthopper(*Laodelphax striatellus*), brown rice planthopper(*Nilaparvata lugens*), whitebacked rice planthopper(*Sogatella furcifera*), etc.; leafhoppers (Deltocephalidae) such as green rice leafhopper (*Nephotettix cincticeps*), zig-zag rice leafhopper (*Recilia dorsalis*), green rice leafhopper (*Nephotettix virescens*), etc.; aphids (Aphididae), plant bugs (Alydidae. Coreidae, Miridae, Pentatomidae Tingidae, etc.), whiteflies (Aleyrodidae), scale insects (Coccoidea), jumping plantlice (Psyllidae), etc.

Lepidoptera:

Pyralid moths (Pyralidae) such as rice stem borer (*Chilo suppressalis*), rice leafroller (*Cnaphalocrocis medinalis*), Indian meal moth (*Plodia interpunctella*), etc.; owlet moths (Noctuidae) such as common cutworm (*Spodoptera litura*), rice armyworm (*Pseudaletia separata*), cabbage armyworm (*Mamestra brassicae*), etc.; whites (Pieridae) such as common cabbage worm (*Pieris rapae crucivora*), etc.; bell moths (Tortricidae) such as Adoxophyes spp.,etc; Carposinidae; lyonetiid moths (Lyonetiidae); tussock moths (Lymantriidae); plusiid moths (Plusiinae); Agrotis spp. such as turnip moth (*Agrotis segetum*), black cutworm (*Agrotis ipsilon*), etc.; Heliothis spp.; diamondback moth (*Plutella xylostella*), casemaking clothes moth (*Tinea translucens*), webbing clothes moth (*Tineola bisselliella*), etc.

Diptera:

House mosquitoes (Culex spp.) such as common mosquito (*Culex pipiens pallens*), *Culex tritaeniorhychus*, etc.; Aedes spp. such as *Aedes aegypti*, *Aedes albopictus*, etc.; Anophelinae such as *Anopheles sinensis*, etc.; midges (Chironomidae);

Muscidae such as houseflies (*Musca domestica*), false stableflies (*Muscina stabulans*), lesser houseflies (*Fannia canicularis*). etc.; blow flies (Calliphoridae); flesh flies (Sarcophagidae); anthomyiid flies (Anthomyiidae) such as seedcorn maggot (*Delia platura*), onion maggot (*Delia antigua*), etc.; fruit flies (Tephritidae); small fruit flies (Drosophilidae); moth flies (Psychodidae); tabanid flies (Tabanidae); black flies (Simuliidae); stable flies (Stomoxyidae), etc.

Beetles (Coleoptera):

Corn rootworms (Diabrotica) such as western corn rootworm (*Diabrotica virgifera*), southern corn rootworm (*Diabrotica undecimpunctata*), etc.; scarabs (Scarabaeidae) such as cupreous chafer (*Anomala cuprea*), soybean beetle (*Anomala rufocuprea*), etc.; weevils (Curculionidae) such as rice water weevil (*Lissorhoptrus oryzophilus*), etc.; Rhynchophoridae such as maize weevil (*Sitophilus zeamais*), etc.; darking beetles (Tenebrionidae) such as yellow mealworm (*Tenebrio molitor*), red flour beetle (*Tribolium castaneum*), etc.; leaf beetles (Chrysomelidae) such as striped flea beetle (*Phyllotreta striolata*), cucurbit leaf beetle (*Aulacophora femoralis*), etc.; deathwatch and drugstore beetles (Anobiidae); Epilachna spp. such as twenty-eight-spotted ladybird (*Epilachna vigintioctopunctata*), etc.; powderpost beetles (Lyctidae); false powderpost beetles (Bostrychidae); longicorn beetles (Cerambycidae); robe beetles (*Paederus fuscipes*); etc.

Cockroaches (Dictyoptera):

German cockroach (*Blattella germanica*), smokybrown cockroach (*Periplaneta fuliginosa*), American cockroach (*Periplaneta americana*), brown cockroach (*Periplaneta brunnea*), oriental cockroach (*Blatta orientalis*), etc.

Thrips (Thysanoptera):

Thrips palmi, flower thrips (*Thrips hawaiiensis*, etc.;

Hymenoptera:

Ants (Formicidae), hornets (Vespidae), bethylid wasps (Bethylidae), sawflies (Tenthredinidae) such as cabbage sawfly (*Athalia rosae ruficornis*), etc.

Orthoptera:

Mole crickets (Gryllotalpidae), grasshoppers (Acrididae), etc.

Fleas (Siphonaptera):

*Purex irritans*, etc.

Sucking lice (Anoplura):

*Pediculus humanus, Pthirus pubis*, etc., and Termites (Isoptera):

*Reticulitermes speratus*, Formosan subterranean termite (*Coptotermes formosanus*), etc.

Noxious mites and ticks such as:

Spidermites (Tetranychidae):

Carmine spider mite (*Tetranychus cinnabarinus*), two-spotted spider mite (*Tetranychus urticae*), Kanzawa spider mite (*Tetranychus kanzawai*), citrus red mite (*Panonychus citri*), European red mite (*Panonychus ulmi*), etc.

Ixodidae:

*Boophilus microplus*, etc., and House dust mites:

Acaridae, Pyroglyphidae, Cheyletidae, Dermanyssidae, etc.

When the present compounds are used as an active ingredient of the pesticidal agent, it is a common practice to formulate them into the various formulations described below by mixing with a solid carrier, a liquid carrier, a gaseous carrier or a bait, or by impregnating them into base materials such as mosquito coils, mosquito mats, etc., and if necessary by adding surface active agents and other auxiliaries for formulation. The above formulations include oil sprays, emulsifiable concentrates, wettable powders, flowable formulations such as, for example, water-based suspension formulations, water-based emulsion formulations, etc, granules, dusts, aerosols, heating smoking formulations such as, for example, mosquito coils, electric mosquito mats, electric non-mat formulations, etc., heating smoking formulations such as, for example, self-combustible smoking formulations, chemically reactive smoking formulations, porous ceramic plate-form smoking formulations, etc., non-heating volatile formulations such as, for example, resin volatile formulations, impregnated paper volatile formulations, etc., foggings, ULV formulations, poisonous baits and the like.

These formulations usually contain the present compound as an active ingredient in an amount of 0.001% to 95% by weight.

The solid carrier used in formulation includes, for example, fine powders or granules of clays (e.g. kaolin clay, diatomaceous earth, synthetic hydrated silicon oxide, bentonite, Fubasami clay, acid clay), talcs, ceramics, other inorganic minerals (e.g. sericites, quartz, sulfur, active carbon, calcium carbonate, hydrated silica) and chemical fertilizers (e.g. ammonium sulfate, ammonium phosphate, ammonium nitrate, urea, ammonium chloride). The liquid carrier includes, for example, water, alcohols (e.g. methanol, ethanol), ketones (e.g. acetone, methyl ethyl ketone), aromatic hydrocarbons (e.g. benzene, toluene, xylene, ethylbenzene, methylnaphthalene), aliphatic hydrocarbons (e.g. hexane, cyclohexane, kerosene, gas oil), esters (e.g. ethyl acetate, butyl acetate), nitriles (e.g. acetonitrile, isobutyronitrile), ethers (e.g. diisopropyl ether, dioxane), acid amides (e.g. N,N dimethylformamide, N,N-dimethylacetamide), halogenated hydrocarbons (e.g. dichloromethane, trichloroethane, carbon tetrachloride), dimethyl sulfoxide, vegetable oils (e.g. soybean oil, cotton seed oil), etc. The gaseous carrier. i.e. a propellant, includes, for example, flon gas, butane gas, LPG (liquefied petroleum gas), dimethyl ether, carbon dioxide gas and the like.

The surface active agents include, for example, alkyl sulfates, alkylsulfonates, alkylarylsulfonates, alkyl aryl ethers and their polyoxyethylenated products, polyethylene glycol ethers, polyhydric alcohol esters, sugar alcohol derivatives and the like.

The auxiliaries for formulation such as fixing agents, dispersing agents, etc. include, for example, casein, gelatin, polysaccharides (e.g. starch powder, gum arabic, cellulose derivatives, alginic acid), lignin derivatives, bentonite, saccharides, synthetic water soluble polymers (e.g. polyvinyl alcohol, polyvinyl pyrrolidone, polyacrylic acids), etc. The stabilizing agents include, for example, PAP (isopropyl acid phosphate), BET (2,6-di-tert-butyl-4-methylphenol), BHA (a mixture of 2-tert-butyl-4-methoxyphenol and 3-tert butyl-4-methoxyphenol), vegetable oils, mineral oils, surface active agents, fatty acids and their esters, and the like.

The base material for the mosquito coils includes, for example, mixtures of a vegetable raw powder (e.g. wood powder, pyrethrum marc) with a binder (e.g. tabu powder, starch, gluten).

The base material for the electric mosquito mats includes, for example, plate-like hardened products of fibrils of cotton linter or a mixture of cotton linter and pulp.

The base material for the self-combustible smoking formulations includes, for example, combustible exothermic agents (e.g. nitrates, nitrites, guanidine salts, potassium chlorate, nitro-cellulose, ethyl cellulose, wood powders), pyrolysis-stimulating agents (e.g. alkali metal salts, alkaline earth metal salts, dichromates, chromates), oxygen-supplying agents (e.g. potassium nitrate), combustion assistants (e.g. melamine, wheat starch), fillers (e.g. diatomaceous earth) and binders (e.g. synthetic pastes).

The base-material for the chemically reactive smoking formulations includes, for example, exothermic agents (e.g. sulfides, polysulfides, hydrosulfides and hydrate salts of alkali metals, calcium oxide) catalysts (e.g. carbonaceous substances, iron carbide, activated clay), organic foaming agents (e.g. azodicarbonamide, benzenesulfonylhydrazide, dinitrosopentamethylenetetramine, polystyrene, polyurethane) and fillers (e.g. natural fiber pieces, synthetic fiber pieces).

The base material for the non-heating volatile formulations includes, for example, thermoplatic resins, filter paper and Japanese paper.

The base material for the poisonous baits include, for example, bait components (e.g. grain powders, vegetable oils, saccharides, crystalline cellulose), antioxidant (e.g. dibutylhydroxytoluene, nordihydroguaiaretic acid), preservers(e.g. dehydroacetic acid), substances for preventing erroneous eating (e.g. red pepper powder), and attractants (e.g. cheese perfume, onion perfume, peanut oil).

Flowable formulations (water-based suspension or emulsion formulations) are generally obtained by finely dispersing 1 to 75% of the present compound in water containing 0.5 to 15% of a dispersing agent. 0.1 to 10% of a suspension assistant (e.g. protective colloids, compounds giving thixotropy) and 0 to 10% of a suitable auxiliary (e.g. antifoaming agents, anti corrosives, stabilizers, spreading agents, penetration auxiliaries, antifreezing agents, antibacterial agents, antimolding agents). It is also possible to obtain oil based suspension formulations by replacing water by an oil in which the present compound is almost insoluble. The protective colloids include, for example, gelatin, casein, gums, cellulose esters, polyvinyl alcohol, etc., and the compounds giving thixotropy include, for example, bentonite, aluminum magnesium silicate, xanthane gum, polyacrylic acid and the like.

The formulations thus obtained are used as they are or diluted with water, etc. They may also be used in mixture with other insecticides, acaricides, nematicides, soil-pest controlling agents, fungicides. herbicides, plant growth regulators, synergists, fertilizers, soil improvers, etc., or may be used together with these chemicals simultaneously and without mixing.

Examples of the insecticides and acaricides used herein include, for example, the following:

Organophosphorus compounds such as fenitrothion [O,O-dimethyl O-(3-methyl-4-nitrophenyl) phosphorothioate], fenthion [O,O-dimethyl O-(3-methyl-4-(methylthio)phenyl) -phosphorothioate], diazinon [O,O-diethyl-O-2-isopropyl-6-methylpyrimidin-4-ylphosphorothioate], chlorpyriphos [O,O-diethyl-O-3,5,6-trichloro-2-pyridylphosphorothioate], DDVP [2,2-dichlorovinyl-dimethylphosphate], etc.; carbamate compounds such as BPMC [2-sec-butylphenyl methylcarbamate], propoxur [2-isopropoxyphenyl N-methylcarbamate], etc.; pyrethroid compounds such as ethofenprox [2-(4-ethoxyphenyl)-2-methylpropyl-3-phenoxybenzyl ether], fenvalerate [(RS)-α-cyano-3-phenoxybenzyl (RS)-2-(4-chlorophenyl)-3-methylbutyrate], esfenvalerate [(S)-α-cyano-3-phenoxybenzyl (S)-2-(4-chlorophenyl)-3-methylbutyrate], fenpropathrin [(RS)-α-cyano-3-phenoxybenzyl 2,2,3,3-tetramethylcyclopropanecarboxylate], cypermethrin [(RS)-α-cyano-3-phenoxybenzyl (1RS-cis, trans)-3-(2,2-dichlorovinyl)-2,2-dimethylcyclopropanecarboxylate], permethrin [3-phenoxybenzyl (1RS-cis, trans)-3-(2,2-dichlorovinyl)-2, 2-dimethylcyclopropanecarboxylate], deltamethrin [(S)-α-cyano-3-phenoxybenzyl (1R-cis)-3-(2,2-dibromovinyl)-2,2-dimethylcyclopropanecarboxylate], halfenprox [2-methyl-2-(4-bromodifluoromethoxyphenyl)propyl (3-phenoxybenzyl) ether], tralomethrin [(1R-cis) 3-[(1RS) (1',2',2',2'-tetrabromoethyl)]-2,2-dimethylcyclopropanecarboxylic acid (S)-α-cyano-3-phenoxybenzyl ester], silafluofen [4-ethoxyphenyl {3-(4-fluoro-3-phenoxyphenyl)-propyl} dimethylsilane], d-phenothrin [3-phenoxybenzyl (1R-cis, trans)-chrysanthemate], cyphenothrin[(RS)-α-cyano-3-phenoxybenzyl (1R-cis,trans)-chrysanthemate], d-resmethrin [5-benzyl-3-furylmethyl(1R-cis, trans)-chrysanthemate], acrinathrin [(S)-α-cyano-3-phenoxybenzyl (1R-cis(Z))-(2,2-dimethyl-3-{3-oxo-3-(1,1,1,3,3,3-hexafluoropropyloxy)-propenyl}-cyclopropanecarboxylate], cyfluthrin[(RS) -α-cyano-4-fluoro-3-phenoxybenzyl 3-(2,2-dichlorovinyl)-2,2-dimethylcyclopropanecarboxylate], lambdahalothrin [(RS)-α-cyano-3-phenoxybenzyl (1RS-cis(Z))-3-(2-chloro-3,3,3-trifluoroprop-1-enyl)-2,2-dimethylcyclopropanecarboxylate], tefluthrin[2,3,5,6-tetrafluoro-4-methylbenzyl (1RS-cis(Z))-3-(2-chloro-3,3,3-trifluoroprop-1-enyl)-2,2-dimethylcyclopropanecarboxylate], transfluthrin [2,3,5,6-tetrafluorobenzyl (1R-trans)-3-(2,2-dichlorovinyl)-2,2-dimethylcyclopropane-carboxylate], prallethrin [(S)-2-methyl-4-oxo-3-(2-propynyl)-2-cyclopenten-1-yl (1R-cis, trans)-chrysanthemate], d-allethrin [2-methyl-4-oxo-3-(2-propenyl)- 2-cyclopenten-1-yl (1R-cis,trans)-chrysanthemate], d-tetramethrin [3,4,5,6-tetraphthalimidomethyl (1R-cis,trans)-chrysanthemate] etc.; and nitroimidazolidine derivatives such as imidachloprid [1-(6-chloro-3-pyridylmethyl)-N-nitroimidazolidin-2-ylidenamine], etc., and benzoylphenylurea compounds such as chlorofluazuron [1-(3,5-dichloro-4-(3-chloro-5-trifluoromethyl pyridin-2-yloxy)phenyl)-3-(2,6-difluorobenzoyl)urea], teflubenzuron [1-(3,5-dichloro-2,4-difluorophenyl)-3-(2,6-difluorobenzoyl)urea], flufenoxuron [1-(4-(2-chloro-4-trifluoromethylphenoxy)-2-fluorophenyl)-3-(2,6-difluorobenzoyl)-urea], etc.

When the present compounds are used as an active ingredient for the pesticidal agents used in agriculture, their dosage rate is usually 0.1 to 500 g/10 ares. When the emulsifiable concentrates, wettable powders, flowable formulations, etc. are used diluted with water, the application concentration of the active ingredient is from 0.1 to 1000 ppm. The granules, dusts, etc., are used as they are without being diluted. When the present compounds are used as an active ingredient for the pesticidal agents used for household and public hygiene, the emulsifiable concentrates, wettable powders, flowable formulations, etc., are appllied diluted with water to 0.1 to 10000 ppm, and the oil sprays, aerosols, fumigants, smoking formulations, volatile formulations, foggings, ULV formulations, poisonous baits, etc., are applied as they are.

Any of these dosage rate and application concentration vary with the kind of formulations, when, where and how these formulations are applied. the kind of pests, the degree of damage, etc., and therefore they may be increased or decreased independently of the ranges described above.

The present invention will be illustrated in more detail with reference to the following preparation examples, formulation examples and test examples, but it is not limited to these examples.

PRODUCTION EXAMPLE 1

1.7 Mililiters of thionyl chloride, and catalytic amount of DMF were added to a dry benzene solution of 4.576 g of (E)-(1R,cis)-2,2-dimethyl-3-[2-fluoro-2-(ethoxycarbonyl)-ethenyl]cyclopropane-1-carboxylic acid and reacted under reflux for 2 hours. The reaction solution was concentrated under reduced pressure to obtain the corresponding carboxylic acid chloride. 3.986 g of 5-methyl-4-propargyl-2,4-dihydro-3H-1,2,4-triazol-3-on-2-ylmethyl alcohol, 4.2 ml of triethylamine and catalytic amount of 4-dimethylaminopyridine were dissolved in 30 ml of dry THF and cooled to 0° C. To the resulting solution were added 10 ml of THF solution of carboxylic acid chloride prepared above and the resulting solution was stirred for 14 hours at room temperature. The reaction solution was poured into a saturated ammonium chloride solution and extracted three times with diethyl ether. The combined organic layer was washed with brine and separated organic layer was dried over anhydrous magnesium sulfate. The filtered solution was evaporated under reduced pressure to give a crude product. The product was purified with silica gel column chromatography (eluent; n-hexane: ethyl acetate=3:1(v/v)) to give 6.39g of 5-methyl-4-propargyl-2,4-dihydro-3H-1,2, 4-triazol-3-on-2-ylmethyl (E)-(1R, cis)-2,2-dimethyl-3-[2-fluoro-2-(ethoxycarbonyl)etheryl]cyclopropane-1-carboxylate (present compound (1)).

$^1$H-NMR (CDCl$_3$solvent, TMS as internal standard, 250 MHz)

δ value(ppm): 5.89(q, 1H), 5.21(dd, 2H), 4.44(d, 2H), 4.30 (q, 2E), 2.88(brt, 1H), 2.37(m, 1H), 2.36(s, 3H), 1.91(d, 1H), 1.36(t, 3H), 1.26(s, 3H), 1.25(s, 3H).

PRODUCTION EXAMPLE 2

0.08 Mililiters of thionyl chloride, and catalytic amount of DMF were added to a dry benzene solution of 0.183 g of (Z)-(1R,cis)-2,2-dimethyl-3-[2-(ethoxycarbonyl)ethenyl]-cyclopropane-1-carboxylic acid and reacted under reflux for 2 hours. The reaction solution was concentrated under reduced pressure to obtain the corresponding carboxylic acid chloride. 0.188 g of 5-methyl-4-propargyl-2,4-dihydro-3H-1,2,4-triazol-3-on-2-ylmethyl alcohol, 0.23 ml of triethylamine and catalytic amount of 4-dimethylaminopyridine were dissolved in 5 ml of dry THF and cooled to 0° C. To the resulting solution were added 2 ml of THF solution of carboxylic acid chloride prepared above and the resulting solution was stirred for 15 hours at room temperature. The reaction solution was poured into a saturated ammonium chloride solution and extracted three times with diethyl ether. The combined organic layer was washed with brine and separated organic layer was dried over anhydrous magnesium sulfate. The filtered solution was evaporated under reduced pressure to give a crude product. The product was purified with silica gel column chromatography (eluent; n-hexane: ethyl acetate=3:1(v/v)) to give 0.287 g of 5-methyl-4-propargyl-2,4-dihydro-3H-1,2,4-triazol-3-on-2-ylmethyl (Z)-(1R, cis)-2,2-dimethyl-3-[2-(ethoxycarbonyl)-ethenyl]cyclopropane-1-carboxylate (present compound (2)).

$^1$H-NMR (CDCl$_3$solvent, TMS as internal standard, 250 MHz)

δ value(ppm): 6.60(brt, 1H), 5.89(d, 1H), 5.73(d, 1H), 5.68(d, 1H), 4.44(d, 2H), 4.17(q, 2H), 3.28(brt, 1H), 2.35 (brs, 1H), 2.35(s, 3H), 1.94(d, 1H), 1.30(s, 3H), 1.29(t,3H), 1.26(s,3H).

Some of the present compounds and their compound numbers are listed below:

(1) 5-methyl-4-propargyl-2,4-dihydro-3H-1,2,4-triazol-3-on-2-ylmethyl (E)-(1R, cis)-2,2-dimethyl-3-[2-fluoro-2-(ethoxycarbonyl)ethenyl]cyclopropane-1-carboxylate, (2) 5-methyl-4-propargyl-2,4-dihydro-3H-1,2,4-triazol-3-on-2-ylmethyl (Z)-(1R, cis)-2,2-dimethyl-3-[2-(ethoxycarbonyl)-ethenyl]cyclopropane-1-carboxylate, (3) 5-methyl-4-propargyl-2,4-dihydro-3H-1,2,4-triazol-3-on-2-ylmethyl (Z)-(1R, cis)-2,2-dimethyl-3-[3-oxo-3-{(2,2,2-trifluoro-1-(trifluoromethyl)ethoxy}-1-propenyl]cyclopropane-1-carboxylate, and (4) 2-propargyl-2,4-dihydro-3H-1,2,4-triazol-3-on-4-ylmethyl (E)-(1R, cis)-2,2-dimethyl-3-[2-fluoro-2-(ethoxycarbonyl)-ethenyl]cyclopropane-1-carboxylate.

Formulation examples will be shown below. In the examples, part is by weight, and the present compounds will be shown by the compound numbers shown above.

FORMULATION EXAMPLE 1

Emulsifiable Concentrates

Twenty parts of each of the compounds (1) to (4) are dissolved in 65 parts of xylene, and 15 parts of Sorpol 3005X, an emulsifier (a registered trade mark of Toho Kagaku Co., Ltd.) are added thereto. The resulting mixture is well stirred and mixed to obtain a 20% emulsifiable concentrate of each compound.

FORMULATION EXAMPLE 2

Wettable Powders

To 40 parts of each of the compounds (1) to (4) are added 5 parts of Sorpol 3005X (described above), and after well stirring, 32 parts of Carplex #80, finely powdered synthetic hydrated silicon oxide (a registered trade mark of Shionogi Seiyaku Co., Ltd.) and 23 parts of 300-mesh diatomaceous earth are added thereto. The resulting mixture is well stirred and mixed with a juice mixer to obtain a 40% wettable powder of each compound.

FORMULATION EXAMPLE 3

Granules 1.5 Parts of each of the compounds (1) to (4) and 98.5 parts of AGSORB LVM-MS24/48, a calcined product of montmorillonite (a granular carrier of 24 to 48 mesh in particle size; produced by OIL DR1 Co., Ltd.), are well mixed to obtain a 1.5% granule of each compound.

FORMULATION EXAMPLE 4

Microencapsulated Formulations

Ten parts of each of the compounds (1) to (4), 10 parts of phenylxylylethane and 0.5 part of Sumidur L-75, tolylene-diisocyanate (produced by Sumitomo Bayer Urethane Co., Ltd.) are mixed. The resulting mixture is added to 20 parts of a 10% aqueous gum arabic solution and stirred with a homomixer to obtain an emulsion of 20 µm in average particle size..Thereafter, 2 parts of ethylene glycol is added thereto and reaction is carried out for 24 hours at 60° C. in a warm bath to obtain a microcapsule slurry. Separately, 0.2 part of xanthane gum and 1.0 part of Veegum R. aluminum magnesium silicate (produced by Sanyo Kasei Co., Ltd.), are dispersed in 56.3 parts of ion-exchanged water to obtain a thickening agent solution. 42.5 Parts of the above microcapsule slurry and 57.5 parts of the above thickening agent solution are mixed to obtain a 10% microencapsulated formulation of each compound.

FORMULATION EXAMPLE 5

Flowable Formulations

Ten parts of each of the compounds (1) to (4) and 10 parts of phenylxylylethane are mixed and added to 20 parts of a 10% aqueous polyethylene glycol solution and stirred with a homomixer to obtain an emulsion of 3 µm in average particle size. Separately, 0.2 part of xanthane gum and 1.0 part of Veegum R, aluminum magnesium silicate (produced by Sanyo Kasei Co.,Ltd.), are dispersed in 58.8 parts of ion-exchanged water to obtain a thickening agent solution. Forty parts of the above emulsion and 60 parts of the above thickening agent solution are mixed to obtain a 10% flowable formulation of each compound.

FORMULATION EXAMPLE 6

Dusts

Five parts of each of the compounds (1) to (4), 3 parts of Carplex #80 (described above), 0.3 part of PAP and 91.7 parts of 300-mesh talc are mixed with stirring with a juice mixer to obtain a 5% dust of each compound.

FORMULATION EXAMPLE 7

Oil Solutions 0.1 Part of each of the compounds (1) to (4) is dissolved in 5 parts of dichloromethane, and mixed with 94.9 parts of deodorized kerosene to obtain a 0.1% oil solution of each compound.

FORMULATION EXAMPLE 8

Oil-based Aerosols

One part of each of the compounds (1) to (4), 5 parts of dichloromethane and 34 parts of a deodorized kerosene are mixed into a solution. The resulting solution is put in an aerosol container. After attaching a valve part to the container. 60 Parts of a propellant (liquefied petroleum gas) is charged into the container under pressure through the valve part to obtain an oil-based aerosol of each compound.

FORMULATION EXAMPLE 9

Water-based Aerosols 0.6 Part of each of the compounds (1) to (4), 5 parts of xylene 3.4 parts of a deodorized kerosene and 1 part of an emulsifier, Atoms 300 (a registered trade mark of Atlas Chemical Co., Ltd.) are mixed into a solution. The resulting solution and 50 parts of pure water are put in an aerosol container. After attaching a valve part to the container, 40 parts of a propellant (liquefied petroleum gas) is charged into the container under pressure through the valve part to obtain a water-based aerosol of each compound.

FORMULATION EXAMPLE 10

Mosquito Coils 0.3 Gram of each of the compounds (1) to (4) is dissolved in 20 ml of acetone and uniformly mixed with 99.7 g of a mosquito coil carrier (a mixture of tabu powder, pyrethrum marc and wood powder in a weight ratio of 4:3:3) with stirring. After adding 120 ml of water to the resulting mixture, the mixture is well kneaded, shaped into a mosquito coil and dried to obtain a mosquito coil of each compound.

FORMULATION EXAMPLE 11

Electric Mosquito Mat Formulations 0.8 Gram of each of the compounds (1) to (4) and 0.4 g of piperonyl butoxide are dissolved in acetone, and the total volume of the solution is made up to 10 ml with acetone. Thereafter, 0.5 ml of this solution is uniformly impregnated into a base material for electric mats of 2.5 cm×1.5 cm×0.3 cm (thickness) (a plate-like hardened product of fibrils of a mixture of cotton linter and pulp) to obtain an electric mosquito mat formulation of each compound.

FORMULATION EXAMPLE 12

Electric Mosquito Liquid Formulations

Three parts of each of the compounds (1) to (4) are dissolved in 97 parts of a deodorized kerosene and put in a vinyl chloride container. A liquid absorbing core (a sintered product of an inorganic powder hardened with a binder), of which the upper part is made so that it can be heated with a heater, is inserted into the container to obtain an electric mosquito liquid formulation of each compound.

FORMULATION EXAMPLE 13

Heating Smoking Formulation

One hundred milligrams of each of the compounds (1) to (4) are dissolved in a suitable amount of acetone, and impregnated into a porous ceramic plate of 4.0 cm×4.0 cm×1.2 cm (thickness) to obtain a heating smoking formulation of each compound.

FORMULATION EXAMPLE 14

Room-temperature Volatile Formulations

One hundred μg of each of the compounds (1) to (4) are dissolved in a suitable amount of acetone, and uniformly coated onto a filter paper of 2 cm×2 cm×0.3 mm (thickness). Acetone is removed by air-drying to obtain a room-temperature volatile formulation of each compound.

FORMULATION EXAMPLE 15

Mite-controlling Sheets

An acetone solution of each of the compounds (1) to (4) is dropped to a filter paper and impregnated into the paper so that the amount of the compound is 1 g per m². Acetone is removed by air-drying to obtain a mite-controlling sheet of each compound.

Test examples will be shown for the purpose of showing that the present compound is useful as an active ingredient of pesticidal agents. The present compounds are shown by the foregoing compound numbers, and compounds used as a control are shown by the compound symbol in Table 3.

TABLE 3

| Compound | Chemical formula | Remarks |
| --- | --- | --- |
| (A) | $HC{\equiv}CCH_2-N(\text{...})N-CH_2OCCH-CHCH=C(Cl)(Cl)$ (with $CH_3$, $CH_3$, $CH_3$ substituents) | 1R-trans isomer of Compound (1) disclosed in Kokai Sho 57-158765 |

TEST EXAMPLE 1

Ten adults (five males and five females) of german cockroach (*Blattella germanica*) were liberated in a polyethylene cup having a diameter of 9 cm of which the inner wall surface was thinly coated with margarine and covered with 16-mesh nylon gauze. The cup was placed in a bottom of a cylinder made of acryl having an inside diameter of 10 cm and a height of 37 cm. Thereafter, 0.6 ml of the 0.003% oil solution of test compound obtained according to Formulation Example 7 was directly sprayed from the top of the cylinder under a pressure of 0.6 atm by means of a spray gun. After 1 minute, the number of the knocked-down insects was examined (two replicate). The results are shown in Table 4.

TABLE 4

| Compound | Percentage of knocked-down insects (%) |
| --- | --- |
| (1) | 100 |
| (A) | 35 |

TEST EXAMPLE 2

Ten female adults of common mosquito (Culex pipiens pallens) were liberated in a 70 cm cube (0.34 m³) glass chamber. Thereafter, 0.7 ml of the 0.0125% oil solution of each test compound obtained according to Formulation Example 7 was sprayed into the chamber under pressure of 0.8 atm by means of a spray gun. After 0.6 minute the number of the knocked-down insects was examined. The results are shown in Table 5.

TABLE 5

| Compound | Percentage of knocked down-insects (%) |
| --- | --- |
| (1) | 90 |
| (A) | 16 |

We claim:

1. An ester compound of the formula (I),

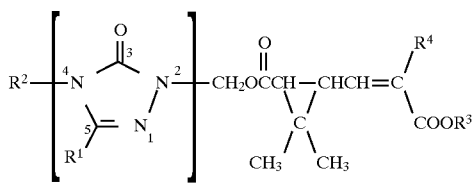

wherein $R^1$ represents a methyl group or a hydrogen atom, $R^2$ represents a propargyl group or an allyl group, and $R^3$ represents a ($C_1$–$C_5$)alkyl group, a ($C_1$–$C_5$)haloalkyl group or a ($C_3$–$C_5$)cycloalkyl group and $R^4$ represents a halogen atom or a hydrogen atom.

2. An ester compound according to claim 1, wherein $R^2$ represents a propargyl group.

3. An ester compound according to claim 1, wherein $R^4$ represents a fluorine atom, a chorine atom, or a bromine atom.

4. An ester compound according to claim 1, wherein $R^4$ represents a fluorine atom.

5. An ester compound according to claim 1, wherein the substituent group $R^2$ is on the 4-position of the triazolone ring of the formula I.

6. An ester compound according to claim 1, wherein the $COOR^3$ group and cyclopropane ring are in cis-configuration with respect to the double bond to which they are bonded.

7. An ester compound according to claim 1, which is (1) 5-methyl-4-propargyl-2,4-dihydro-3H-1,2,4-triazol-3-on-2-ylmethyl (E)-(1R, cis)-2,2-dimethyl-3-[2-fluoro-2-(ethoxycarbonyl)ethenyl]cyclopropane-1-carboxylate, (2) 5-methyl-4-propargyl-2,4-dihydro-3H-1,2,4-triazol-3-on-2-ylmethyl (Z)-(1R, cis)-2,2-dimethyl-3-[2-(ethoxycarbonyl)-ethenyl]cyclopropane-1-carboxylate, (3) 5-methyl-4-propargyl-2,4-dihydro-3H-1,2,4-triazol-3-on-2-ylmethyl (Z)-(1R, cis)-2,2-dimethyl-3-[3-oxo-3-{(2,2,2-trifluoro-1-(trifluoromethyl)ethoxy}-1-propenyl]cyclopropane-1-carboxylate, or (4) 2-propargyl-2,4-dihydro-3H-1,2,4-triazol-3-on-4-ylmethyl (E)-(1R, cis)-2,2-dimethyl-3-[2-fluoro-2-(ethoxycarbonyl)-ethenyl]cyclopropane-1-carboxylate.

8. A method for controlling noxious insects or acarines, which comprises applying an insecticidally or acaricidally effective amount of an ester compound of formula (I)

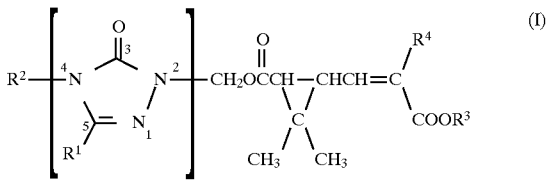

to a locus where noxious insects and/or acarines propagate, wherein $R^1$ represents a methyl group or a hydrogen atom, $R^2$ represents a propargyl group or an allyl group, and $R^3$ represents a ($C_1$–$C_5$) alkyl group, a ($C_1$–$C_5$) haloalkyl croup or a ($C_3$–$C_5$) cycloalkyl group and $R^4$ represents a halogen atom or a hydrogen atom.

9. An insecticide or acarcide composition comprising an ester compound of formula (I):

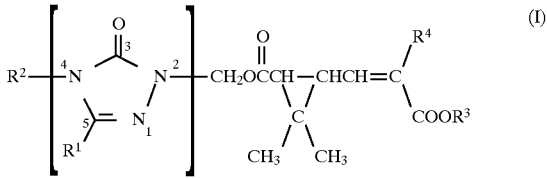

wherein $R^1$ represents a methyl group or a hydrogen atom, $R^2$ represents a propargyl group or an allyl group, and $R^3$ represents a ($C_1$–$C_5$) alkyl group, a ($C_1$–$C_5$) haloalkyl group or a ($C_3$–$C_5$) cycloalkyl group and $R^4$ represents a halogen atom or a hydrogen atom, the formula (I) compound contained as an active ingredient in an amount of 0.001% to 95% by weight and an inert carrier.

* * * * *